United States Patent [19]

Genova et al.

[11] Patent Number: 5,597,576
[45] Date of Patent: Jan. 28, 1997

[54] OIL-BASED TRANSPARENT GELS

[75] Inventors: Calogero Genova, Vizzolo Predabissi; Francesco Buosi, Milan; Sandra Guarnerio, Cusano Milanino, all of Italy

[73] Assignee: Enichem Augusta Industriale S.r.l., Milan, Italy

[21] Appl. No.: 274,447

[22] Filed: Jul. 13, 1994

[30] Foreign Application Priority Data

Jul. 21, 1993 [IT] Italy .................. MI93A1610

[51] Int. Cl.$^6$ ...................................... A61K 7/00
[52] U.S. Cl. .......................................... 424/401; 514/944
[58] Field of Search ............... 424/401, 65; 514/944, 514/844

[56] References Cited

U.S. PATENT DOCUMENTS

| | | | |
|---|---|---|---|
| 4,078,147 | 3/1978 | Ukai et al. | 560/180 |
| 4,840,788 | 6/1989 | Beachell | 424/59 |
| 5,000,945 | 3/1991 | Kabayashi | 424/59 |
| 5,073,573 | 12/1991 | Martin | 514/844 |
| 5,141,964 | 8/1992 | Noel | 514/777 |
| 5,258,136 | 11/1993 | Smith | 252/315.4 |

FOREIGN PATENT DOCUMENTS 0357186  3/1990  European Pat. Off. .

OTHER PUBLICATIONS

Database WPI, Week 7647, Derwent Publications Ltd., London, GB; AN 76–87425X & JP–A–50 082 103 (Nisshin Oils Mills KK) Jul. 3, 1975.

Chemical Abstracts, vol. 117, No. 10, Sep. 7, 1992, Columbus, Ohio, US; abstract No. 97110f, T. Shoko "transparent oily cosmetic gels" & JP–A–4 059 716 (Noebia K.K.) Feb. 26, 1992.

*Primary Examiner*—Gollamudi S. Kishore
*Attorney, Agent, or Firm*— Oblon, Spivak, McClelland, Maier & Neustadt, P.C.

[57]  ABSTRACT

Oil-based gels are described containing tartaric or malic acid diesters possibly mixed with oils, and other components such as silica and polyalcohols. The gels are characterized by a wide viscosity range and can find application in the preparation of formulations for cosmetics and pharmaceutical use.

11 Claims, No Drawings

OIL-BASED TRANSPARENT GELS

This invention relates to oil-based transparent gels characterised by a wide viscosity range, for use in the pharmaceutical and cosmetics sectors.

The gels contain tartaric acid or malic acid diesters of $C_{12}$–$C_{13}$ single-branch fatty alcohols, possibly mixed with oils and other compounds such as silica and polyalcohols.

Lipogels are physico-chemical structures which, if obtained in clear form, enable formulations to be prepared having a consistency similar to or even better than creams or modern gel emulsions, without the use of cellulose methacrylic polymers or other compounds typical of aqueous systems.

Transparent lipogels have a particularly pleasing appearance, and compared with aqueous formulations have the advantage of not requiring preservatives and of being able to be used in very small quantity.

Another important advantage of lipogels is the ability to obtain lipid structures with differing performance in terms of skin feeling, greasiness and the possibility of inserting liposoluble and water-soluble active principles, these being characteristics which facilitate the development of final applications.

However the preparation of gels with the required properties is not always easy.

The literature describes various processes for preparing transparent lipogels.

For example, Japanese patent 63223083 describes the preparation of transparent lipogels by heating mixtures formed from terpenes, paraffins and/or polyalcohols (oil base) and ionic surfactants deriving from fatty acids to 80° C., followed by slow cooling. The need to heat the mixtures results however in a considerable increase in the preparation costs of such formulations.

Japanese patent 4059716 describes transparent lipogels prepared by cold-mixing pyrogenic silica with a non-ionic surfactant and a oily component consisting of a malic ester and olive oil. The formulations obtained have however only a moderate viscosity (7.5 Pa.s) which limits their use for specific applications. An alternative method consists of using the vegetable origin gelling agent for oily components known by the commercial name of GP-100®, marketed by Ajinomoto, which enables transparent gels to be obtained without the presence of adjuvants. However the preparation method again comprises heating the mixture to about 80°–85° C. In addition the gelling agent cost is high and the consistency of the gels obtained is rather low.

We have now found that it is possible to obtain transparent lipogels characterised by a wide viscosity range by mixing tartaric or malic acid esters, possibly containing oils or any cosmetics excipient, with other compounds such as silica and polyalcohols under cold conditions, in determined proportions.

The present invention therefore provides transparent lipogels for cosmetics and pharmaceutical use having the following composition:

A) an ester chosen from:
  tartaric acid diester of $C_{12}$–$C_{13}$ single-branch fatty alcohols in a quantity of between 46 and 95 wt %,
  malic acid diester of $C_{12}$–$C_{13}$ single-branch fatty alcohols in a quantity of between 87 and 93 wt %;

B) an oil or ester chosen from:
  2-ethyl-hexanoic acid alkyl ($C_{12}$–$C_{13}$ single-branch) ester,
  2-hydroxy-1,2,3-propanetricarboxylic acid alkyl ($C_{12}$–$C_{13}$ single-branch) triester,
  white oil,
  jojoba oil,
  benzophenone-6,
  ethylhexyl-p-methoxy-cinnamate,
  sweet almond oil, in a quantity of between 1 and 46%;

C) hydrophilic or hydrophobic pyrogenic silica in a quantity of between 2.8 and 7.0%;

D) a polyalcohol chosen from:
  polyethyleneglycol 200 (PEG),
  ethyleneglycol,
  1,2-propyleneglycol,
  glycerin, in a quantity of between 1 and 10%.

The viscosity of the gels of our invention varies considerably in relation to the composition of the different systems and can be regulated on the basis of the type of silica and type of co-gelling agent (polyalcohol), hence enabling the field of final applications to be widened.

The tartaric or malic acid diesters of $C_{12}$–$C_{13}$ single-branch fatty alcohols are completely compatible with the most widely used cosmetics excipients in the preparation of formulations, even in high proportion (1:1, w/w), these including for example white oils, vegetable oils (jojoba, sweet almond), solid and liquid solar filters (EU-SOLEX and PARSOL CMX respectively) and Cosmacol esters (EOI and ECI).

It should also be noted that the dermotoxicological safety of the key products (Cosmacol esters, silica and glycols) makes these gels a useful addition for the formulator in ensuring certain success of both cosmetics and pharmaceutical preparations. Their possible uses in the cosmetics sector include the preparation of protective products, such as:

Sun creams with a predetermined sun protection factor

Water-repellent creams for professional use

Hand barrier creams

Face and lip creams, particularly protective for sensitive skin

Manual massage creams

Body products such as anticellulitis, etc.

In addition gels and detergents for the hair, hands and body can be prepared, as well as bath oils.

In the pharmaceutical sector, because of their special properties these lipogels can replace traditional ointments with considerable advantages, including bioavailability.

For example all topical medicaments can be formulated as lipogels, which have the advantage of making their application more pleasant than traditional ointment formulations.

Topical medicaments can consequently be prepared with corticosteroids or antimycotics, or galenic preparations be produced containing sulphur, zinc oxide, resorcinol, ichthyol etc. In specific or general antimycotic, antiseptic and detergent preparations they contribute considerably to the active principle, with no interference with preservatives.

The lipogels of the present invention could also be of interest for other products, such as shoe creams, wood polishing products, hand washing pastes and in other sectors where solid or semi-solid lipid structures are required.

All the components used in preparing the formulations are available commercially, and specifically:

the tartaric acid diester of $C_{12}$–$C_{13}$ single-branch fatty alcohols is known by the name COSMACOL ETI® and is marketed by ENICHEM AUGUSTA INDUSTRIALE, Milan;

The malic acid diester of $C_{12}$–$C_{13}$ single-branch fatty alcohols is known by the name COSMACOL EMI® and is marketed by ENICHEM AUGUSTA INDUSTRIALE, Milan;

the 2-ethyl-hexanoic acid alkyl ($C_{12}$–$C_{13}$ single-branch) ester is known by the name COSMACOL EOI® and is marketed by ENICHEM AUGUSTA INDUSTRIALE, Milan;

the 2-hydroxy-1,2,3-propanetricarboxylic acid alkyl ($C_{12}$–$C_{13}$ single-branch) triester is known by the name COSMACOL ECI® and is marketed by ENICHEM AUGUSTA INDUSTRIALE, Milan;

benzophenone-6 is known by the name EUSOLEX® 4360 and is marketed by MERCK;

ethylhexyl-p-methoxy-cinnamate is known by the name PARSOL MCX® and is marketed by GIVAUDAN.

The transparent gels are prepared under cold conditions by mild mechanical agitation. Heating to 35°–40° C. is necessary only if glycerin is used.

It is also possible to prepare a base (consisting of Cosmacol ester and pyrogenic silica in the desired concentration) having the characteristics of a transparent viscous fluid, to which the various cosmetics excipients are added until a final formulation suitable for the required type of application is obtained.

In this case, the last stage of the preparation consists of adding the co-gelling agent (polyalcohols) in the desired quantity, followed by agitation of the mixture.

The obtaining of transparent gels is strictly dependent on the type of lipo-gelling agent used and on the chosen oil base. In addition there seems to be a particular compatibility between the esters of our invention and the various types of polyalcohol. In this respect, low polyalcohol concentrations are generally sufficient to obtain a transparent system. The required concentration is 1–2% on average.

The pyrogenic silica can be used either as such (hence hydrophilic) or silanized (hence hydrophobic). The minimum pyrogenic silica concentration which enables transparent gels to be obtained is less than 3 wt % for the hydrophilic type, whereas for the silanized type (hydrophobic) it is greater than 3.5 wt % but less than 5 wt %.

The viscosity of the formulations was determined by a BROOKFIELD rotary viscometer fitted with an RV=7 spindle at a spindle speed of 50 rpm or 20 rpm, the appearance of the formulations being evaluated visually.

The following examples are given to better illustrate the present invention and are not to be considered as limitative of its scope, which is defined by the accompanying claims.

EXAMPLE 1

100 g of the composition ET19 according to the invention were prepared, it consisting of:
a) 85.8 g of COSMACOL ETI
b) 4.5 g of HYDROPHILIC PYROGENIC SILICA (WACKER HDK V15)
c) 4.7 g of COSMACOL EOI
d) 5.0 g of 1,2-PROPYLENEGLYCOL The composition was prepared by mixing components a and b together under cold conditions using a mechanical stirrer or turboagitator. While agitating the obtained homogeneous solution with a turbomixer at moderate speed, component c and finally component d were added.

The appearance of the obtained compositions was determined visually: F=fluid, GT=transparent gel, GO=opaque gel. The viscosity (expressed in Pascal/second) was determined as described on page 6.

EXAMPLE 2

Following the procedure described in Example 1, a series of lipogels were prepared having the composition and viscosity and transparency characteristics given in the following tables (1-1a-1b-1c-1d-2-2a-2b).

The results show that only by mixing the components in determined proportions is it possible to obtain transparent formulations of particular viscosity.

The formulations with the required properties are marked with an asterisk.

TABLE 1

| Component | LIPOGELS WITH COSMACOL ETI | | | | | | | | | | |
|---|---|---|---|---|---|---|---|---|---|---|---|
| | ET1 | ET2 | ET3 | ET4 | ET5 | ET6 | ET7 | ET8 | ET9 | ET10 | ET11 |
| | | | | | % by weight | | | | | | |
| Cosmacol ETI | 96 | 93.1 | 91.1 | 96.5 | 93.1 | 90.2 | 87.4 | 85.5 | 94.0 | 93.6 | 92.1 |
| Hydrophobic silica | 2 | 1.9 | 1.9 | 2.0 | 4.9 | 4.8 | 4.6 | 4.5 | 5.0 | 4.9 | 6.9 |
| PEG 200 | 2 | 5 | 7 | — | 2 | 5 | 8 | 10 | 1 | — | 1 |
| Glycerin | — | — | — | 1.5 | — | — | — | — | — | 1.5 | — |
| APPEARANCE | F | F | F | F | GT* | GT* | GT* | GT* | GT* | G0 | GT* |
| VISCOSITY | | | | | | | | | | | |
| (50 rpm) | | | | | 15.2 | 14.0 | 12.8 | 11.6 | 12,0 | 10.8 | 37.6 |
| (20 rpm,) | 3.2 | 3.0 | 3.0 | 2.0 | | | | | | | |

TABLE 1a

| Component | LIPOGELS WITH COSMACOL ETI | | | | | | | | | |
|---|---|---|---|---|---|---|---|---|---|---|
| | ET12 | ET13 | ET14 | ET15 | ET16 | ET17 | ET18 | ET38 | ET39 | ET40 |
| | | | | | % by weight | | | | | |
| Cosmacol ETI | 91.1 | 90.2 | 85.6 | 95.5 | 91.7 | 93.1 | 90.2 | 92.1 | 92.1 | 92.1 |
| Hydrophobic silica | 6.9 | 6.8 | 6.4 | 3.5 | 3.3 | 4.9 | 4.8 | — | — | — |
| Hydrophilic silica | — | — | — | — | — | — | — | 6.9 | 6.9 | 6.9 |
| PEG 200 | 2 | 3 | 8 | 1 | 5 | — | — | 1 | — | — |
| Propyleneglycol | — | — | — | — | — | 2 | 5 | — | 1 | — |
| Glycerin | — | — | — | 1.5 | — | — | — | — | — | 1 |
| APPEARANCE | GT* | GT* | GT* | F | F | F | F | GT* | GT* | GT* |

TABLE 1a-continued

LIPOGELS WITH COSMACOL ETI

| Component | ET12 | ET13 | ET14 | ET15 | ET16 | ET17 | ET18 | ET38 | ET39 | ET40 |
|---|---|---|---|---|---|---|---|---|---|---|
| | | | | | % by weight | | | | | |
| VISCOSITY | | | | | | | | | | |
| (50 rpm) | 36.0 | 32.0 | 25.6 | — | — | — | — | 68.0 | 36.8 | 64.0 |
| (20 rpm) | | | | 5.0 | 5.8 | 5.0 | 7.5 | | | |

TABLE 1b

LIPOGELS WITH COSMACOL ETI

| Component | ET20 | ET21 | ET22 | ET23 | ET24 | ET25 | ET26 | ET27 | ET28 |
|---|---|---|---|---|---|---|---|---|---|
| | | | | | % by weight | | | | |
| Cosmacol ETI | 90.4 | 90.8 | 89.5 | 90.9 | 90.6 | 95.0 | 94.1 | 93.6 | 89.0 |
| Hydrophilic silica | 4.8 | 4.5 | 5.5 | 38 | 3.9 | 4.0 | 3.9 | 3.9 | 3.9 |
| PEG 200 | 4.8 | 4.8 | 5.0 | — | — | — | — | — | — |
| Propyleneglycol | — | — | — | 5.4 | — | — | — | — | 7.2 |
| Glycerin | — | — | — | — | 1.5 | 1.0 | 2.0 | 2.5 | — |
| APPEARANCE | GT* | GT* | GT* | GT* | GT* | GT* | GT* | GT* | GT* |
| VISCOSITY (50 rpm) | 18.4 | 13.5 | 21.6 | — | 25.0 | 20.0 | 18.0 | 26.5 | — |

TABLE 1c

LIPOGELS WITH COSMACOL ETI

| Component | ET19 | ET29 | ET30 | ET31 | ET32 | ET33 | ET34 | ET35 | ET36 |
|---|---|---|---|---|---|---|---|---|---|
| | | | | | % by weight | | | | |
| Cosmacol ETI | 85.8 | 88.5 | 88.5 | 88.5 | 88.5 | 95.5 | 94.9 | 93.8 | 89.2 |
| Hydrophobic silica | — | 4.7 | 4.7 | 4.7 | 4.7 | — | — | — | — |
| Hydrophilic silica | 5.0 | — | — | — | — | 3.0 | 2.9 | 2.9 | 2.8 |
| PEG 200 | 4.5 | 2.0 | 2.0 | 2.0 | 2.0 | — | 2.2 | — | — |
| Propyleneglycol | — | — | — | — | — | — | — | 3.3 | 3.2 |
| Glycerin | — | — | — | — | — | 1.5 | — | — | — |
| Cosmacol EOI | 4.7 | — | — | — | — | — | — | — | — |
| Cosmacol ECI | — | 4.9 | — | — | — | — | — | — | — |
| White oil | — | — | — | 4.9 | — | — | — | — | — |
| Jojoba oil | — | — | 4.9 | — | — | — | — | — | 4.8 |
| Eusolex 4360 | — | — | — | — | 4.9 | — | — | — | — |
| APPEARANCE | GT* | GT* | GT* | GT* | GT* | GT* | GT* | GT* | GT* |
| VISCOSITY (50 rpm) | 22.5 | 13.2 | 16.0 | 13.6 | 13.0 | 10.4 | 8.0 | 6.5 | 5.6 |

TABLE 1d

LIPOGELS WITH COSMACOL ETI

| Component | ET37 | ET41 | ET42 | ET43 | ET45 | ET46 | ET47 | ET48 |
|---|---|---|---|---|---|---|---|---|
| | | | | | % by weight | | | |
| Cosmacol ETI | 89.2 | 87.5 | 91.1 | 83.7 | 46.0 | 46.0 | 46.0 | 46.0 |
| Hydrophilic silica | 2.8 | 6.6 | 6.9 | 6.3 | 3.5 | 3.2 | 3.2 | 3.2 |
| PEG 200 | — | 1.0 | — | — | 1.0 | — | 1.0 | — |
| Propyleneglycol | 3.2 | — | 1.0 | 0.9 | — | 1.0 | — | 1.0 |
| White oil | 4.8 | — | — | — | 49.5 | 49.5 | — | — |
| Jojoba oil | — | — | — | — | — | — | 49.5 | 49.5 |
| Almond oil | — | 4.0 | — | — | — | — | — | — |
| Eusolex 4360 | — | — | 1 | — | — | — | — | — |
| Parsol MCX | — | — | — | 9.0 | — | — | — | — |
| APPEARANCE | GT* | GT* | GT* | GT* | GT* | GT* | GT* | GT* |
| VISCOSITY (50 rpm) | 5.2 | 63.0 | 60.0 | 20.0 | 8.0 | 7.2 | 7.6 | 6.4 |

TABLE 2

TRANSPARENT GELS WITH COSMACOL EMI

| Component | EM1 | EM2 | EM3 | EM4 | EM5 | EM6 | EM7 | EM8 | EM9 | EM10 | EM11 |
|---|---|---|---|---|---|---|---|---|---|---|---|
| | | | | | | % by weight | | | | | |
| Cosmacol EMI | 92.9 | 90.2 | 87.4 | 93.6 | 93.1 | 89.8 | 91.7 | 96.0 | 93.1 | 90.2 | 94.1 |
| Hydrophobic silica | 4.9 | 4.8 | 4.6 | 4.9 | 4.9 | 4.7 | 4.8 | 2.0 | 1.9 | 1.8 | 4.9 |
| PEG 200 | 2.2 | 5.0 | 8.0 | — | — | — | — | 2.0 | 5.0 | 8.0 | 1.0 |
| Glycerin | — | — | — | 1.5 | — | — | — | — | — | — | — |
| Ethylene glycol | — | — | — | — | 2.0 | 5.5 | 3.5 | — | — | — | — |
| APPEARANCE | GT* | GT* | GT* | G0 | GT* | G0* | G0* | F | F | F | GT* |
| VISCOSITY | | | | | | | | | | | |
| (50 rpm) | 12.0 | 12.0 | 16.0 | 10.5 | 12.0 | 7.2 | 13.6 | — | — | — | 8.0 |
| (20 rpm,) | — | — | — | — | — | — | — | 2.5 | 2.5 | 2.5 | — |

TABLE 2a

TRANSPARENT GELS WITH COSMACOL EMI

| Component | EM12 | EM13 | EM18 | EM19 | EM20 |
|---|---|---|---|---|---|
| | | | % by weight | | |
| Cosmacol EMI | 90.3 | 90.2 | 88.4 | 91.0 | 92.2 |
| Hydrophilic silica | 4.7 | 5.1 | 6.7 | 6.9 | 6.9 |
| PEG 200 | 5.0 | 4.7 | — | 2.2 | — |
| Glycerin | — | — | — | — | 0.9 |
| Propylene glycol | — | — | 4.9 | — | — |
| APPEARANCE | GT* | GT* | F | GT* | G0 |
| VISCOSITY | | | | | |
| (50 rpm) | 23.0 | 11.0 | — | 4.8 | 7.6 |
| (20 rpm,) | — | — | 6.0 | — | — |

TABLE 2b

TRANSPARENT GELS WITH COSMACOL EMI

| Component | EM14 | EM15 | EM17 |
|---|---|---|---|
| | | % by weight | |
| Cosmacol EMI | 88.5 | 88.5 | 88.5 |
| Hydrophobic silica | 4.7 | 4.7 | 4.7 |
| PEG 200 | 2.0 | 2.0 | 2.0 |
| Cosmacol ECI | 4.9 | — | — |
| Jojoba oil | — | 4.9 | — |
| White oil | — | — | 4.9 |
| APPEARANCE | GT* | GT* | GT* |
| VISCOSITY | | | |
| (50 rpm) | 7.2 | 7.6 | 6.0 |
| (20 rpm,) | — | — | — |

We claim:

1. A transparent lipogel formulation for cosmetic and pharmaceutical use, characterised by a viscosity of between 4.8 and 68 Pa.s and consisting essentially of:

A) an ester selected from the group consisting of:
—tartaric acid diester of $C_{12}$–$C_{13}$ single-branch fatty alcohols in a quantity of between 46 and 95 wt %, and
—malic acid diester of $C_{12}$–$C_{13}$ single-branch fatty alcohols in a quantity of between 87 and 95 wt %;

B) an oil or ester selected from the group consisting of:
—2-ethyl-hexanoic acid alkyl ($C_{12}$–$C_{13}$ single-branch) ester,
—2-hydroxy-1,2,3-propanetricarboxylic acid alkyl ($C_{12}$–$C_{13}$ single-branch) triester,
—white oil,
—jojoba oil,
—benzophenone-6
—ethylhexyl-p-methoxy-cinnamate, and
—sweet almond oil,
in a quantity of between 0 and 46 wt %;

C) hydrophilic or hydrophobic pyrogenic silica in a quantity of between 2.8 and 7.0 wt. %;

D) a polyalcohol selected from the group consisting of:
—polyethyleneglycol 200 (PEG),
—ethyleneglycol,
—1,2-propyleneglycol, and
—glycerin,
in a quantity of between 1 and 10 wt %, said components A), B), C) and D) being present in amounts that result in a transparent lipogel.

2. A formulation in accordance with claim 1, characterised by a viscosity of between 11 and 36 Pa.s and having the following composition:

A) tartaric acid diester of $C_{12}$–$C_{13}$ single-branch fatty alcohols in a quantity of between 85 and 95 wt %;

C) hydrophobic pyrogenic silica in a quantity of between 4.5 and 7.0 wt %;

D) polyethyleneglycol 200 in a quantity of between 2 and 10 wt %.

3. A formulation in accordance with claim 1, characterised by a viscosity of between 13 and 68 Pa.s and having the following composition:

A) tartaric acid diester of $C_{12}$–$C_{13}$ single-branch fatty alcohols in a quantity of between 89 and 95 wt %;

C) hydrophilic pyrogenic silica in a quantity of between 3.6 and 7.0 wt %;

D) polyethyleneglycol 200 in a quantity of between 1 and 5 wt %.

4. A formulation in accordance with claim 1, characterised by a viscosity of between 13 and 68 Pa.s and having the following composition:

A) tartaric acid diester of $C_{12}$–$C_{13}$ single-branch fatty alcohols in a quantity of between 89 and 96 wt %;

C) hydrophilic pyrogenic silica in a quantity of between 3.9 and 4.0 wt %;

D) glycerin in a quantity of between 1 and 2.5 wt %.

5. A formulation in accordance with claim 1, characterised by a viscosity of between 13 and 68 Pa.s and having the following composition:

A) tartaric acid diester of $C_{12}$–$C_{13}$ single-branch fatty alcohols 89.0 wt %

C) hydrophilic pyrogenic silica 3.9 wt %

D) 1,2-propyleneglycol 7.2 wt %.

6. A formulation in accordance with claim 1, characterised by a viscosity of 22.5 Pa.s and having the following composition:

A) tartaric acid diester of $C_{12}$–$C_{13}$ single-branch fatty alcohols 85.8 wt %

B) 2-ethyl-hexanoic acid alkyl ($C_{12}$–$C_{13}$ single-branch) ester 4.7 wt %

C) hydrophilic pyrogenic silica 5.0 wt %

D) polyethyleneglycol 200 4.5 wt %.

7. A formulation in accordance with claim 1, characterised by a viscosity of between 13.0 and 16 Pa.s and having the following composition:

A) tartaric acid diester of $C_{12}$–$C_{13}$ single-branch fatty alcohols 88.5 wt %

B) an oil or ester selected from the group consisting of:
—2-hydroxy-1,2,3-propanetricarboxylic acid alkyl ($C_{12}$–$C_{13}$ single-branch) triester,
—benzophenone-6,
—white oil, and
—jojoba oil, in a quantity of 4.9 wt %;

C) hydrophobic pyrogenic silica 4.7 wt %

D) polyethyleneglycol 200 2.0 wt %.

8. A formulation in accordance with claim 1, characterised by a viscosity of between 5.2 and 63 Pa.s and having the following composition:

A) tartaric acid diester of $C_{12}$–$C_{13}$ single-branch fatty alcohols in a quantity of between 46 and 95.5 wt %;

B) an oil or ester selected from the group consisting of:
—white oil,
—jojoba oil,
—benzophenone-6, and
—ethylhexyl-p-methoxy-cinnamate, in a quantity of between 1 and 49.5 wt. %;

C) hydrophilic pyrogenic silica in a quantity of between 2.9 and 6.9 wt %;

D) a polyalcohol selected from the group consisting of:
—polyethyleneglycol 200,
—1,2-propyleneglycol, and
—glycerin, in a quantity of between 1 and 3.3 wt %.

9. A formulation in accordance with claim 1, characterised by viscosity of between 12 and 16 Pa.s and having the following composition:

A) malic acid diester of $C_{12}$–$C_{13}$ single-branch fatty alcohols in a quantity of between 90.2 and 94.1 wt %;

C) hydrophobic pyrogenic silica in a quantity of between 4.6 and 4.9 wt %;

D) a polyalcohol selected from the group consisting of:
—polyethyleneglycol 200, and
—ethyleneglycol, in a quantity of between 2 and 8 wt %.

10. A formulation in accordance with claim 1, characterised by a viscosity of between 4.8 and 23.0 Pa.s and having the following composition:

A) malic acid diester of $C_{12}$–$C_{13}$ single-branch fatty alcohols in a quantity of between 90.2 and 94.1 wt %;

C) hydrophilic pyrogenic silica in a quantity of between 4.7 and 6.9 wt %;

D) polyethyleneglycol 200, in a quantity of between 4.8 and 23 wt %.

11. A formulation in accordance with claim 1, characterised by a viscosity of between 6.0 and 7.6 Pa.s and having the following composition:

A) malic acid diester of $C_{12}$–$C_{13}$ single-branch fatty alcohols in a quantity of 88.5 wt %;

B) an oil or ester selected from the group consisting of:
—2-hydroxy-1,2,3-propanetricarboxylic acid alkyl ($C_{12}$–$C_{13}$ single-branch) triester,
—white oil, and
—jojoba oil, in a quantity of 4.9 wt %;

C) hydrophobic pyrogenic silica in a quantity of 4.7 wt %;

D) polyethyleneglycol 200, in a quantity of 2 wt %.

* * * * *